United States Patent [19]

Wakunaga et al.

[11] Patent Number: 4,686,185

[45] Date of Patent: Aug. 11, 1987

[54] MICROORGANISM OF NEW SPECIES OF GENUS STREPTOMYCES AND USE THEREOF FOR PRODUCTION OF CHITINASE

[75] Inventors: Manji Wakunaga, Toyonaka; Yasufumi Nishimura, Hiroshima, both of Japan

[73] Assignee: Wakunaga Kono Kabushiki Kaisha, Takata, Japan

[21] Appl. No.: 759,293

[22] Filed: Jul. 26, 1985

[30] Foreign Application Priority Data

Aug. 2, 1984 [JP] Japan ............................. 59-163237
Aug. 2, 1984 [JP] Japan ............................. 59-163238

[51] Int. Cl.⁴ ..................... C12N 9/36; C12N 1/20; C13L 3/00; C12R 1/465; C12P 19/28

[52] U.S. Cl. ............................ 435/206; 435/253; 435/274; 435/886; 435/85

[58] Field of Search ............... 435/206, 253, 274, 85

[56] References Cited

PUBLICATIONS

Hirano et al., Agric. Biol. Chem. 44(4), 963–964 (1980).
Tominaga et al., Agric. Biol. Chem. 40(12), 2325–2333 (1976).

*Primary Examiner*—Lionel M. Shapiro
*Attorney, Agent, or Firm*—Oblon, Fisher, Spivak, McClelland & Maier

[57] ABSTRACT

A microorganism of a new species of the genus Streptomyces having an ability to produce chitinase has been found, and a method of producing chitinase using this microorganism is disclosed.

3 Claims, 6 Drawing Figures

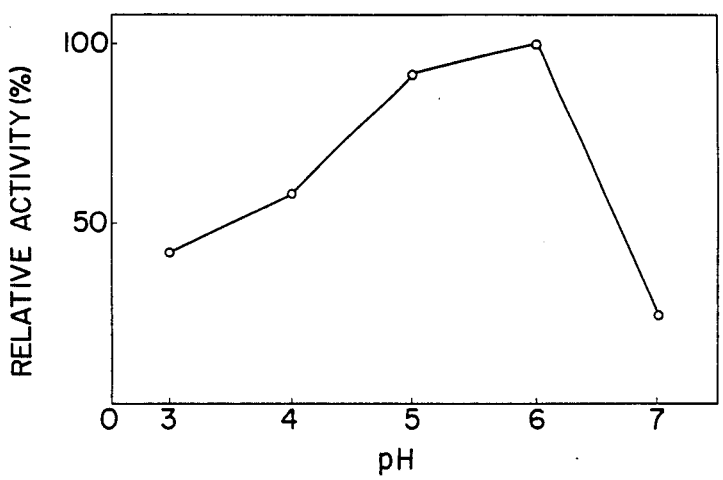
F I G. 4
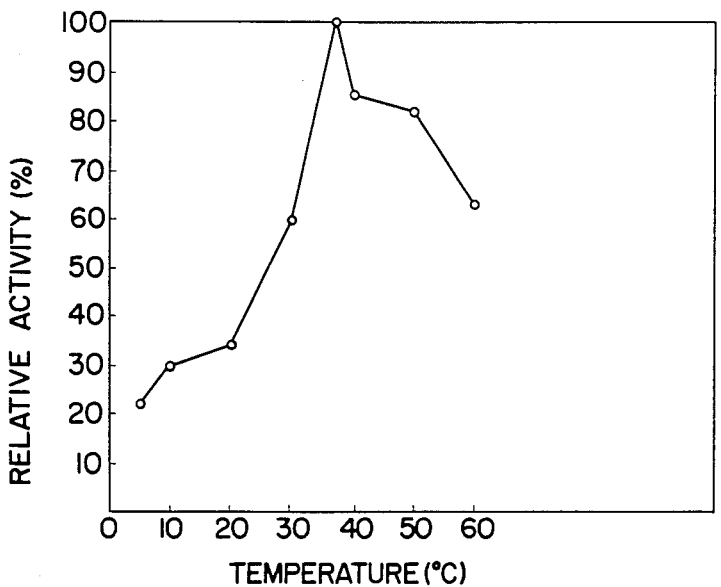
F I G. 5

MICROORGANISM OF NEW SPECIES OF GENUS STREPTOMYCES AND USE THEREOF FOR PRODUCTION OF CHITINASE

BACKGROUND OF THE INVENTION

1. Technical Field

The present invention relates generally to microorganisms of the genus Streptomyces and to chitinase and more particularly to a microorganism of a new species of the genus Streptomyces and to a method of producing chitinase therefrom.

Generally, the term "chitinolytic enzyme" refers to a composite enzyme system comprising a variety of enzyme components such as those called chitinase and chitobiase, and the function thereof is to decompose and saccharify chitin even into N-acetyl glucosamine or oligosaccharides.

Chitin is one of polysaccharides belonging to amino sugar and is abundantly contained in lower animals, in particular in arthropods. The quantity of chitin biosynthetically produced annually is so copious as to be estimated at several billion tons, and hence chitin is one of unutilized natural resources that have been in the spotlight in recent years.

Chitin is poorly reactive and more stable than cellulose, so that the decomposition of chitin with an enzyme, i.e., chitinase, into a lower molecular substance may be proposed.

2. Prior Art

Chitinase is contained, for example, in the digestive fluids of snails and is also known to be produced by filamentous fungi or bacteria. (e.g., "Encyclopaedia Chimica" Vol. 2, p. 745, Kyoritsu Shuppan K.K., Tokyo)

According to a catalogue of commercial products, chitinases from microorganism sources are obtained from *Streptomyces griseus* and *Serratia marcescens*. Recently, chitinase derived from microorganisms of the genus Aeromonas is also reported.

SUMMARY OF THE INVENTION

We have searched for microorganisms which produce chitinase highly capable of decomposing powdery chitin and saccharifying the same into N-acetyl glucosamine from among a wide variety of soil samples. As a result, we have found that Streptomyces sp. WAK-83 strain produces and accumulates in a culture medium chitinase having high chitin-decomposing activity coupled with N-acetyl glucosamine-producing ability and have arrived at the present invention on the basis of this finding.

Thus, the chitinase-producing microorganism of a new species of the genus Streptomyces according to the present invention belongs to the species which includes WAK-83 strain of the genus Streptomyces.

The method of producing chitinase in accordance with the present invention comprises culturing a microorganism of a species including WAK-83 strain of the genus Streptomyces.

Chitinase provided by this invention has high chitin-decomposing activity and N-acetyl glucosamine-producing ability.

For this reason, it is possible to decompose chitin advantageously with the chitinase.

BRIEF DESCRIPTION OF THE ILLUSTRATIONS

In the illustrations:

FIGS. 4, 5 and 6 are graphs respectively showing the optimum pH, the optimum temperature, and the stability-retaining temperature range of an enzyme produced from a microorganism of this invention.

DETAILED DESCRIPTION OF THE INVENTION

Microorganism

Figure 1:
FIG. 1 is a photograph of the spore of the Streptomyces sp. WAK-83 of the present invention taken by transmission-type electron microscope.
Figure 2:
FIG. 2 is an optical photomicrograph of the pycnidium produced by the present strain.
Figure 3:
FIG. 3 is an optical photomicrograph of the spore chain of the present strain.
Figure 6:
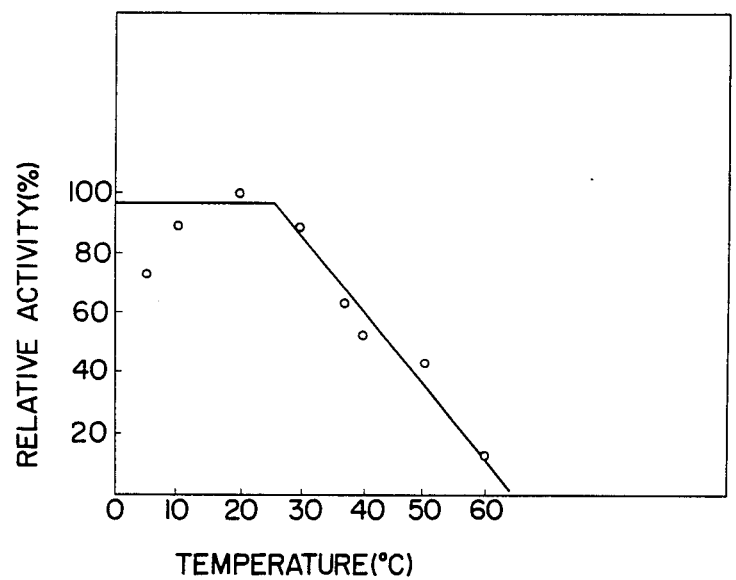

The microorganisms according to the present invention are bacteria of the species to which WAK-83 strain of the genus Streptomyces belongs.

A typical example of the strains of this species is Streptomyces sp. WAK-83 strain. This strain was isolated from the soil in Sukumoji, Kōda-cho, Takata-gun, Hiroshima-ken, Japan in December, 1983, and deposited on July 13, 1984 with the Fermentation Research Institute, Agency of Industrial Science and Technology, Ministry of International Trade and Industry of Japan, 1-3, Higashi 1 chome, Yatabe-machi, Tsukuba-gun, Ibaraki-ken 305, Japan, under Accession No. FERM P-7714, which strain now bears Accession No. FERM BP-826 under the Budapest Treaty on the International Recognition of the Deposit of Microorganisms for the Purposes of Patent Procedure. This depository fully complies with the rules of the Budapest Treaty. Specifically, it fully complies with Rule 11.3 of the Budapest Treaty whereby the organism is available to the public on patent grant and to Rule 9 of the Budapest Treaty which requires the maintenance of the organism for a period of at least 30 years after the date of deposit.

The microbiological characteristics of WAK-83 strain are as follows, color names being assigned according to the Color Name List (Shinju-dō) issued by the Japan Color Research Institute.

I. Morphological Characteristics

WAK-83 strain extends aerial hyphae on various media, which hyphae are branched. No sporangium is formed. Spores are not motile. Mature spores on aerial mycelium are yellow, and a chain of the spores is straight to slightly curved (Rectus Flexibilis). The spores are of a cylindrical shape (2-3 $\mu$m $\times$ 0.8-1.2 $\mu$m), and 20 or more spores form a chain. The surface of the spores is smooth. A salient characteristic of this strain is formation of pycnidium after incubation at 28° C. for fourteen days on Bennett's medium.

II. Cultural Characteristics on Various Media

1. Sucrose-nitrate agar

Good growth with considerable spores. The surface of colonies is yellow, and the reverse rusty red.

2. Glucose-asparagine agar

Abundant growth with abundant spores. The surface of colonies is flesh-colored, and the reverse salmon pink.

3. Glycerol-asparagine agar

Fair growth with fair number of spores. Colonies do not spread very widely. The surface of the colonies is pale yellow, and the reverse salmon pink.

4. Starch-inorganic salts agar

Good growth with considerable spores. The surface of colonies is pale yellow, and the reverse grayish pink.

5. Tyrosine agar

Scant growth with scant spores and fair aerial mycelium. Colonies are not wrinkled. The surface of the colonies is white to pale yellow, and the reverse dull reddish yellowish orange. No soluble pigment.

6. Nutrient agar

White aerial mycelium spreads on yellow substrate mycelium with scant spores. Reverse is yellowish orange.

7. Yeast-malt extract agar

The strain grows in wrinkled state and becomes recurved. The surface of colonies is skin-colored to pale yellow, and the reverse dull reddish yellowish orange.

8. Oatmeal agar

The strain does not grow in wrinkled state. The surface of colonies is white to pale yellow, and the reverse pale yellow.

9. Peptone-yeast extract-iron agar

The strain grows in wrinkled state with scant aerial mycelium and no spores. Both the surface and reverse of colonies are pale orangish brown.

III. Physiological Characteristics

1. Temperature Requirements:

Growth is obtained between 20° and 37° C., the optimum temperature being 28° C. Growth is poor at 37° C.

2. Gelatin liquefaction: Positive
3. Hydrolysis of starch: Positive
4. Growth in milk: No growth
5. Production of melanoid pigment: Negative

IV. Utilization of Carbon Sources

The results obtained by incubation in Pridham-Gottlieb agar medium are as follows.

| Carbon Source | Growth* |
| --- | --- |
| L-arabinose | + |
| D-xylose | + |
| D-glucose | + |
| D-fructose | + |
| Sucrose | + |
| i-inositol | + |
| L-rhamnose | − |
| Raffinose | − |
| D-mannitol | + |
| None added | − |

*+ = growth
− = no growth

V. Identification

In view of the characteristics described above, WAK-83 strain is considered to belong to Streptoyces. The chain of spores is straight to slightly curved; aerial mycelium is white or yellow; the surface of the spores is smooth; and no soluble pigment is produced. According to Bergey's Manual of Determinative Bacteriology, 8th Ed. (1975), this strain may be identified as a strain of Yellow Series (46 species). However, none of the strains of the 46 species forms pycnidium the formation of which is one of salient characteristics of WAK-83 strain, and therefore WAK-83 strain differs from the strains of the 46 species. When strains which form pycnidium are searched for among known strains such as those listed in Bergey's Manual of Determinative Bacteriology, 8th Ed. (1975), ISP strains of Shirling, E. B. and Gottlieb, and strains described in Waksman's The Actinomycetes, *Streptomyces sindenensis* (ISP 5255) is the only strain that forms pycnidium. *Streptomyces sindenensis*, however, forms pink pycnidium while WAK-83 strain forms yellow pycnidium, so that these strains are included in completely different species.

In view of the foregoing, no known strain that was identical with WAK-83 strain was found, and hence this strain was determined to be a strain of a new microorganism species and named Streptomyces sp. WAK-83.

It is possible to further induce from this strain a mutant strain highly capable of producing chitinase in accordance with conventional microorganism mutating methods such as physical treatments by UV-ray, X-ray or γ-ray irradiation or chemical treatments with reagents such as nitrosoguanidine. It is also possible to induce chitinase-producing microorganisms by gene manipulation procedure, for example, by incorporating the gene DNA of the above strain which bears genetic information as to the production of chitinase into an appropriate vector which is in turn transferred by way of transformation into a microorganism of a genus other than Streptomyces, or by permitting the gene DNA to be taken up in a microorganism of another genus by cell fusion. It is to be understood that these microorganisms induced from the above strain are also included within the scope of the present invention.

Cultivation of Microorganism

The present strain can be cultivated by a conventional method for cultivating actinomycetes. A variety of carbon sources such as glucose, starch, fructose, glycerol, and mannitol, singly or in combination, can be incorporated in a culture medium. Examples of nitrogen sources are ammonium chloride, ammonium sulfate, sodium nitrate, soybean meal, yeast extract, peptone, meat extract, and Casamino acid (a product of Difco Laboratories), singly or in combination.

If desired, inorganic salts such as sodium chloride, nitrates, calcium carbonate, potassium chloride, cobalt chloride, iron sulfates, and trace amounts of heavy metals can be added. Some organic substances that encourage the growth of microorganisms to promote the production of chitinase can also be added optionally.

While the present strain can be cultured in a solid culture medium, a liquid medium is preferred as in ordinary methods for producing enzymes. Cultivation is carried out under aerobic conditions generally at a temperature of from 20° C. to 30° C., preferably around 28° C.

Production of chitinase can be accomplished, for example, by tank fermentation. In this case, chitinase is produced and accumulated in the culture fluid after fermentation for 2 to 4 days. When the production yield of chitinase in the culture fluid reaches a maximum, the fermentation is terminated, and the desired chitinase is isolated from the culture and purified as follows.

The resulting culture is centrifuged or filtered with a filter aid to obtain a crude enzyme solution. The fluid obtained by subjecting the culture resulting from the fermentation to centrifugation or filtration to separate cells can be used as a crude enzyme solution without any further treatment, or it can be concentrated to cause sedimentation with an organic solvent such as acetone and ethanol or to cause precipitation with a salting out agent such as ammonium sulfate to obtain a crude enzyme agent. The crude enzyme agent thus obtained can be purified and crystallized by a known method to provide a purified enzyme.

Enzyme Produced

The crude enzyme agent obtained in the manner described above has the following properties.

(1) Activity and Substrate Specificity

This enzyme acts on powdery chitin, chitin flakes, colloidal chitin, or ethylene glycol chitin to decompose it to produce N-acetyl glucosamine. c.f. Table 1 shown hereinlater.

(2) Optimum pH and Stability

The optimum pH at 37° C. is 5.5 to 6.0. This enzyme is stable in the pH range of from 3.5 to 8.0.

(3) Optimum Temperature and Stability

The optimum temperature for the action of this enzyme was 37° C. at a pH of 5.5 in a three-hour reaction. At temperatures of 30° C. or lower, the enzyme was stable over a period of 24 hours or longer.

(4) Purification

Impurities in the crude enzyme agent can be removed by adsorption chromatography over a chitin column, conventional ion-exchange chromatography, or gel filtration with a biogel, whereby a highly purified enzyme agent can be obtained.

The chitinase produced in accordance with the present invention has the advantageous feature of acting on chitin powder more effectively than conventional enzymes. For example, commercial chitinase supplied by Sigma Chemical Co. produces reducing sugar gradually in 48 hours of reaction while the enzyme of this invention is able to produce an equal quantity of reducing sugar in 3 hours of reaction.

Table 1 shows the activity of the chitinase obtained by the present invention with respect to various substrates. The activity was measured for ethylene glycol chitin substantially on the basis of the procedure of Tsukamoto et al. [Agriculture of Biological Chemistry Vol. 48, p. 931 (1984)]. For powdery chitin and chitin gel, the substrates containing 1% each of the powdery chitin and chitin gel were used respectively. The enzymatic activity was determined by the following method for measuring an increase in N-acetyl glucosamine caused by an enzyme reaction (e.g., Morgan-Elson's procedure).

To 1 ml of 1% powdery chitin (supplied by Nakarai Kagaku, Japan) as a substrate were added 1 ml of an enzyme solution at an appropriate concentration and then 3 ml of 0.025M phosphate-acetate buffer solution (pH 5.5) to cause reaction at 37° C. for 3 hours. The quantity of the enzyme which produces 1 μmol/min. of N-acetyl glucosamine under these conditions was defined as 1 unit.

TABLE 1

|  | Chitinase of this invention mU/mg protein |
|---|---|
| Ethylene glycol chitin (Nakarai Kagaku) | 720 |
| Powdery chitin (Nakarai Kagaku) | 4 |
| Chitin gel* | 42 |

*Prepared by the procedure of Hirano et al. ["Biopolymers" Vol. 15, p. 1685 (1976)]

As is apparent from the Table, the chitinase produced in accordance with the present invention effectively decomposes ethylene glycol chitin and chitin gel.

EXPERIMENTAL EXAMPLES

Example

Streptomyces sp. WAK-83 strain was incubated at 28° C. for 4 days on a Bennett's medium slant to which 2.5 ml of sterile water was added to prepare a spore suspension. 2.5 ml of the suspension was inoculated into each of the culture mediums of the following composition respectively placed in 100-ml and 500-ml flasks and subjected to reciprocating shake culture at 28° C. for 3 days.

| Ingredient | Quantity |
|---|---|
| Yeast extract | 3.0 g/liter |
| Polypeptone | 3.0 g/liter |
| Glucose | 2.0 g/liter |
| Colloidal chitin | 4.0 g/liter |

The resulting culture was centrifuged to remove the residue to obtain a crude enzyme solution which showed an enzymatic activity of 1.12 mU/ml on powdery chitin.

Reference Example

Colloidal chitin was prepared as follows.

100 ml of distilled water containing 4 g of powdery chitin and 100 ml of conc. sulfuric acid are separately cooled with ice for 3 hours. After 3 hours, the two solutions are mixed slowly with each other. The mixture is filtered through a funnel filled with glass wool. The filtrate is added to 180 ml of distilled water, and centrifuged at 3,000 rpm. To the residue is added distilled water, and centrifugation is resumed. This operation is repeated until the pH of the wash becomes 6.

What is claimed is:

1. A biologically pure culture of a microorganism selected from the group consisting of Streptomyces sp. WAK-83 (FERM BP-826) and a microorganism derived therefrom.

2. A method of producing chitinase, which comprises culturing a microorganism selected from the group consisting of Streptomyces sp. WAK-83 (FERM BP-826) and a microorganism derived therefrom, on a medium capable of growing said Streptomyces or said microorganism derived therefrom, and collecting said chitinase from the cultured product.

3. A method of decomposing chitin, which comprises contacting said chitin with a chitinase produced by a microorganism selected from the group consisting of Streptomyces sp. WAK-83 (FERM BP-826) and a microorganism derived therefrom.

* * * * *